(12) United States Patent
Singh et al.

(10) Patent No.: US 6,184,395 B1
(45) Date of Patent: Feb. 6, 2001

(54) REACTION CONDITIONS FOR THE CLEAVAGE OF SILYL ETHERS IN THE PREPARATION OF PACLITAXEL(TAXOL®) AND PACLITAXEL ANALOGUES

(75) Inventors: Ambarish K. Singh, Bordentown; Raymond E. Weaver, Hampton; Gerald L. Powers, North Brunswick; Victor W. Rosso, East Windsor, all of NJ (US)

(73) Assignee: Bristol-Myers Squibb Company, Princeton, NJ (US)

(*) Notice: Under 35 U.S.C. 154(b), the term of this patent shall be extended for 0 days.

(21) Appl. No.: 09/571,234

(22) Filed: May 16, 2000

Related U.S. Application Data

(60) Provisional application No. 60/134,469, filed on May 17, 1999.

(51) Int. Cl.[7] .................................................. C07D 305/14
(52) U.S. Cl. ............................................ 549/510; 549/511
(58) Field of Search ..................................... 549/510, 511

(56) References Cited

U.S. PATENT DOCUMENTS

| | | | |
|---|---|---|---|
| Re. 34,277 | 6/1993 | Denis et al. | 549/510 |
| 5,750,738 | 5/1998 | Bastart et al. | 549/510 |

FOREIGN PATENT DOCUMENTS

| | | | |
|---|---|---|---|
| 617018-A1 | 9/1994 | (EP) | C07D/205/08 |
| WO 94/20484 | 9/1994 | (WO) | C07D/305/14 |

OTHER PUBLICATIONS

Greene et al, Protective Groups in Organic Synthesis, Second Edition, 1991, John Wiley & Sons, pp. 68–87.
Wanner et al, SYNLETT, pp. 797–799 (1991).
Chen et al, J. Org, Chem., 58(19), pp. 5028–5029 (1993).
Gennari et al, J. Org. Chem., 62 (14), pp. 4746–4755 (1997).
Marder–Karsenti et al, J. Org. Chem., 62(19), pp. 6631–6637 (1997).
Kelly et al, J. Am. Chem. Soc., 118 (4), pp. 919–920 (1996).
Pulicani et al, Tetrahedron Letters, 35 (52), pp. 9717–9720 (1994).
Ojima et al, Chirality, 9 (5/6), pp. 487–494 (1997).
Ojima et al, Tetrahedron, 52 (1), pp. 209–224 (1996).
Nicolaou et al, J. Chem. Soc. Chem. Commun., (3), pp. 295–296 (1994).

*Primary Examiner*—Ba K. Trinh
(74) *Attorney, Agent, or Firm*—Timothy J. Babcock

(57) ABSTRACT

Novel reaction conditions for the cleavage of silyl ethers from silyl protected taxane precursors to afford paclitaxel and paclitaxel analogues in high yield and quality are described. Paclitaxel is prepared from a taxane precursor by treating the taxane precursor with a strong acid such as trifluoroacetic acid in a solvent such as aqueous acetic acid, such that the amount and number of side reactions and taxane impurities are significantly minimized. Also desribed are the crystallization methods for the isolation of paclitaxel in either of the two crystal forms A or B. Paclitaxel and paclitaxel analogues are anti-cancer agents.

24 Claims, No Drawings

REACTION CONDITIONS FOR THE CLEAVAGE OF SILYL ETHERS IN THE PREPARATION OF PACLITAXEL(TAXOL®) AND PACLITAXEL ANALOGUES

RELATED APPLICATIONS

This application claims priority benefit under Title 35 § 119(e) of U.S. Provisional Application No. 60/134,469, filed May 17, 1999, and entitled NOVEL REACTION CONDITIONS FOR THE CLEAVAGE OF SILYL ETHERS IN THE PREPARATION OF PACLITAXEL (TAXOL®) AND PACLITAXEL ANALOGS.

BRIEF DESCRIPTION OF THE INVENTION

The present invention is directed to reaction conditions for the cleavage of silyl ethers from silyl protected taxane precursors to afford paclitaxel (Taxol®) and paclitaxel analogues. More specifically, the invention is directed to a process for the preparation of paclitaxel from a taxane precursor which comprises the steps of treating the taxane precursor with a strong acid such as trifluoroacetic acid, in a weak aqueous acid, such as aqueous acetic acid, such that the amount and number of side reactions leading to undesirable taxane impurities are minimized, and isolating the product from a solvent that affords paclitaxel in either of the two crystal forms, Form A or Form B.

BACKGROUND OF THE INVENTION

Taxanes are diterpene compounds that find utility in the pharmaceutical field. For example, taxanes containing aryl heterocyclic or cycloalkyl groups on the C-13 sidechain find utility as anti-cancer agents. Taxanes include pacltitaxel, cephalomannine, taxol c, 10-deacetylpaclitaxel, 10-deacetylcephalomannine, 7-β-xylosylpaclitaxel, baccatin-III, 10-deacetylbaccatin III, 7-β-xylosyl-10-deacetyl cephalomannine, 7-β-xylosyl-10-deacetylbaccatin III, 7-β-xylosylbaccatin III, and 10-deacetyl-taxol c.

Paclitaxel (Taxol®), a diterpene taxane compound, is a natural product extracted from the bark of the Pacific yew tree, *Taxus Brevifolia*. It has been shown to have excellent antitumor activity in in vivo animal models, and recent studies have elucidated its unique mode of action, which involves abnormal polymerization of tubulin and disruption of mitosis during the cell cycle. Taxol® has recently been approved for the treatment of refractory advanced ovarian cancer, breast cancer, non-small cell lung cancer, and most recently, AIDS-related Kaposi's Sarcoma. The results of paclitaxel clinical studies are replete in scientific periodicals and have been reviewed by numerous authors, such as Rowinsky and Donehower in "The Clinical Pharmacology and Use of Antimicrotubule Agents in Cancer Chemotherapeutics", *Phamac. Ther.*, 52, pp. 35–84 (1991); Spencer and Faulds, Paclitaxel, A Review of its Pharmacodynamic and Pharmacokinetic Properties and Therapeutic Potential in the Treatment of Cancer, *Drugs*, 48 (5), pp. 794–847 (1994); K. C. Nicolau et al., Chemistry and Biology of Taxol, *Angew. Chem., Int. Ed. Eng.*, 33, pp.15–44 (1994); F. A. Holmes, A. P. Kudelka, J. J. Kavanaugh, M. H. Huber, J. A. Ajani, and V. Valero, "Taxane Anticancer Agents—Basic Science and Current Status", edited by Gunda I. Georg, Thomas C. Chen, Iwao Ojima, and Dolotrai M. Vyas, pp. 31–57 American Chemical Society, Wash., D.C. (1995); Susan G. Arbuck and Barbara Blaylock, "Taxol® Science and Applications", edited by Matthew Suffness, pp. 379416, CRC Press, Boca Raton, Fla. (1995) and the references cited therein.

The structure of Taxol® is shown below along with the conventional numbering system for molecules belonging to the Taxane class; such numbering system is also employed in this application:

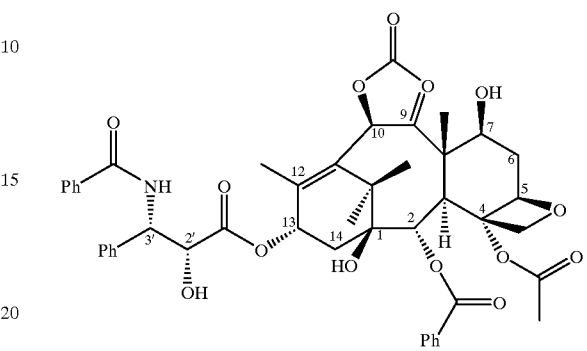

With reference to the numbering of the taxane, reference to a particular carbon on the taxane structure shall be indicated throughout this application by a "C-number", which signifies the carbon on the taxane according to the above numbering system. For example, "C-13" refers to the carbon at position 13 on the taxane ring as shown above, having a sidechain coupled thereto.

Naturally occurring taxanes such as paclitaxel, 10-deacetylpaclitaxel and baccatin III can be extracted from the trunk bark of different species of Taxus (yew). Paclitaxel, in particular, may be extracted from the inner bark of *Taxus brevifolia*. Although *T. brevifolia* is a relatively common tree in the Pacific Northwest, it is a slow growing plant and is indigenous to the ecologically threatened old-growth forests of this area, and harvesting is thus increasingly restricted because of environmental concerns.

As yields of paclitaxel extracted from *T. brevifolia* are generally low, of the order of 100 mg/kg, semisynthetic methods of producing paclitaxel from baccatin III1 and 10-deacetylbaccatin have been developed. Baccatin III, 10-deacetylbaccatin, as well as other paclitaxel precursors may be isolated from the needles of the European yew, Taxus baccata in relatively larger quantities, e.g. approximately 300 mg/kg of 10-deacetylbaccatin may be obtained from yew leaves. Although yew needles generally provide an adequate supply of the necessary starting materials for synthesizing paclitaxel, the supply is not endless and other methods easing the supply dilemma and producing adequate amounts of paclitaxel has become a priority. The art has thus continued to search for synthetic, including semisynthetic routes for the preparation of naturally occurring taxanes such as paclitaxel, as well as the preparation of paclitaxel analogues and second and third generation paclitaxel-like compounds thereof.

Using a semi-synthehic process, paclitaxel may be prepared from numerous paclitaxel precursors, some having protecting groups thereon, particularly at the C-7 postion on the taxane ring and at the 2' position on the sidechain which is connected at position C-13. Paclitaxel may be easily prepared by the deprotection of these paclitaxel precursors.

Several methods for cleaving the silyl ethers have been reported in the literature. However, when applied to silyl protected taxane precursors, most of these procedures generated side reactions and several impurities. In the case of paclitaxel, the most prominent impurity is 10-deacetyltaxol. Some of the other side-reactions known to occur are: opening of the oxetane ring, loss of the C-1 hydroxyl group followed by ring contraction to a 5-membered ring, and epimerization at C-7.

With reference to paclitaxel, this compound exhibits polymorphism. Crystal Form A is predominantly obtained from non-aqueous solvent systems and crystal Form B is predominantly obtained from aqueous solvent systems. Paclitaxel Form A is the preferred crystal form and has been filed with the U.S. Food and Drug Administration.

The present invention relates to novel reaction conditions for the cleavage of silyl ethers from silyl protected taxane precursors that afford high quality paclitaxel and paclitaxel analogues. Also included are crystallization protocols that can afford either of the two paclitaxel crystal forms, Form A or Form B.

DESCRIPTION OF THE INVENTION

The present invention provides a process for the preparation of high quality paclitaxel and paclitaxel analogues from taxanes of formula I:

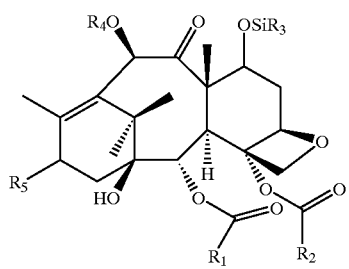

(I)

wherein:

$R_1$=$H_3$, c-$C_6H_{11}$, $C_6H_5$, p-$CH_3$—$C_6H_4$ or p-$NO_2$—$C_6H_4$;

$R_2$=$CH_3$, $CH_2CH_3$, $CH_2CH_2CH_3$, $C(CH_3)_3$, $(CH_2)_3CH_3$, $(CH_2)_4CH_3$, $C_6H_5$, p-$NO_2$—$C_6H_4$, c-$C_3H_5$, c-$C_4H_7$, c-$C_5H_9$, or $OCH_3$;

$R_3$=$(CH(CH_3)_2)_2OCH_3$, $(CH_2CH_3)_3$, $(CH_3)_3$ or $(C(CH_3)_3)(CH_3)_2$;

$R_4$=H, $CH_3$, $C_6H_5$, $COCH_3$, $COC_6H_5$ or $COC_4H_9$;

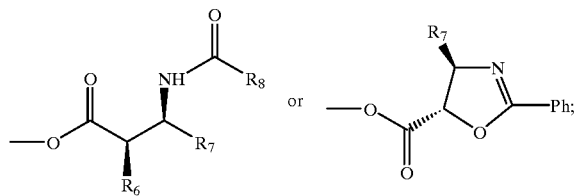

$R_6$=H, F, OH, $OCH_3$, $OSi(CH_2CH_3)_3$, $OSi(C(CH_3)_3)(CH_3)_2$ or $OC(CH_3)_2OCH_3$, provided that $R_6$ is other than $OC(CH_3)_2OCH_3$ when $R_1$ is $C_6H_5$, $R_2$ is $CH_3$, $R_3$ is $(CH_2CH_3)_3$, $R_4$ is $COCH_3$, $R_7$ is $C_6H_5$ and $R_8$ is $C_6H_5$;

$R_7$=$C_6H_5$, $C(CH_3)_3$ or $CH(CH_3)_2$; and $R_8$=$C_6H_5$, $C(CH_3)_3$, $(CH_3)_3CO$, $(CH_3)_3CCH_2$, $CH_3(CH_2)_3O$, cyclobutyl, cyclohexyloxy or 2-furyl.

In accordance herewith, paclitaxel and paclitaxel analogues may be prepared from silyl protected taxane precursors of formula I by a process which comprises the steps of:

(a) preparing a solution of a taxane precursor in a weak organic acid;

(b) preparing a solution comprised of a strong acid in said weak organic acid and water;

(c) adding the solution from step (b) to step (a);

(d) stirring the reaction mixture formed in step (c);

(e) quenching the reaction mixture (to prevent degradation of the product during subsequent processing);

(f) adding water and extracting the product using an organic solvent;

(g) separating the organic layer from the aqueous layer; and (h) isolating the paclitaxel or paclitaxel analogue from the organic layer.

Weak organic acids suitable for use in the present invention include, but are not limited to, $C_1$–$C_6$alkanoic acids such as formic acid, acetic acid, propionic acid and the like. Acetic acid and formic acid are the preferred weak organic acids with acetic acid being more preferred.

Strong acids suitable for use in the process of this invention include, but are not limited to, mineral acids such as hydrochloric acid, sulfuric acid, nitric acid, phosphoric acid and the like; strong organic acids such as trifluoroacetic acid, trichloroacetic acid, methanesulfonic acid, p-toluenesulfonic acid and the like; and strong acid resins such as Amberlyst —15, Nafion and the like. Preferred strong acids include strong organic acids with trifluoroacetic acid being more preferred.

In step (d) of the present invention, the reaction mixture is preferably stirred at ambient temperature until the taxane precursor is consumed.

In a preferred embodiment of the present invention, the volume ratio of the weak organic acid to the water in the reaction mixture is no more than about 3:1.

In step (e) of the process of the invention, the reaction mixture is preferably quenched with a base. Bases suitable for use in this invention include, but are not limited to, alkali metal $C_1$–$C_6$carboxylates such as sodium acetate, potassium acetate and the like; tri($C_1$–$C_4$alcohol)amines such as triethanolamine and the like; and dialkylamines such as diisopropylamine and the like. Preferred bases include alkali metal $C_1$–$C_6$carboxylates with sodium acetate being more preferred.

In another preferred embodiment, the organic solvent used in step (f) of the process of this invention is a water-immiscible organic solvent. Water-immiscible organic solvents suitable for use in this invention include, but are not limited to, halogenated hydrocarbons such as dichloromethane and the like; $C_1$–$C_4$ alkyl $C_1$–$C_6$carboxylates such as ethyl acetate and the like; and ketones such as methyl ethyl ketone, methyl isobutyl ketone and the like; and mixtures thereof. Preferred water-immiscible organic solvents include halogentated hydrocarbons with dichloromethane being more preferred.

Isolation procedures useful in step (h) of this invention include well known conventional procedures including, but not limited to, removal of the organic solvent or addition of an anti-solvent.

In a preferred embodiment of the present invention, taxane precursors of formula I are converted to paclitaxel and paclitaxel analogues of formula II

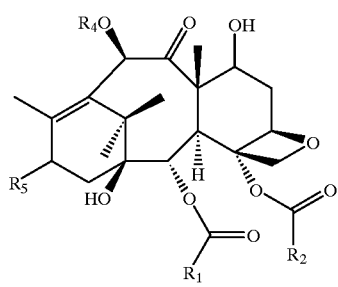

(II)

wherein:

$R_1$=CH$_3$, c-C$_6$H$_{11}$, C$_6$H$_5$, p-CH$_3$—C$_6$H$_4$ or p-NO$_2$—C$_6$H$_4$;

$R_2$=CH$_3$, CH$_2$CH$_3$, CH$_2$CH$_2$CH$_3$, C(CH$_3$)$_3$, (CH$_2$)$_3$CH$_3$, (CH$_3$, (CH$_2$)$_4$CH$_3$, C$_6$H$_5$, p-NO$_2$—C$_6$H$_4$, c-C$_3$H$_5$, c-C$_4$H$_7$, c-C$_5$H$_9$ or OCH$_3$;

$R_4$=H, CH$_3$, C$_6$H$_5$, COCH$_3$, COCH$_5$ or COC$_4$H$_9$; $R_5$=

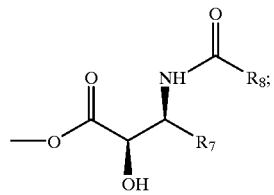

$R_7$=C$_6$H$_5$, C(CH$_3$)$_3$ or CH(CH$_3$)$_2$; and $R_8$=C$_6$H$_5$, C(CH$_3$)$_3$, (CH$_3$)$_3$CO, (CH$_3$)$_3$CCH$_2$, CH$_3$(CH$_2$)$_3$O, cyclobutyl, cyclohexyloxy or 2-furyl.

With reference to paclitaxel, crystal Form A is isolated by solvent exchanging the organic layer from step (h) into an alcohol, such as ethanol, isopropanol or the like, or into a ketone, such as acetone, methyl ethyl ketone, methyl isobutyl ketone or the like, or into an ester, such as ethyl acetate, n-butyl acetate or the like followed by the addition of a hydrocarbon solvent, such as hexane, heptane, cyclohexane or the like, preferably isopropanol followed by heptane. The crystal Form B is isolated by solvent exchanging the organic layer from step (h) into a water-miscible solvent, such as acetic acid, acetone, methanol, ethanol, isopropanol, tetrahydrofuran, acetonitrile or the like followed by the addition of water, preferably acetone or acetic acid followed by the addition of water.

During the crystallization of paclitaxel Form A from isopropanol, the crystal slurry undergoes a phase change. Initially, the crystal slurry remains very thin for several hours, then it undergoes a phase change and it thickens. After 1–2 hours, the slurry thins out again. The yield of the product is low if the slurry is filtered during the early stages of thin phase and the crystal slurry is difficult to filter during the thick phase stage. Therefore, the crystal slurry is filtered only after it has undergone the complete phase transition. Addition of small amounts of water (i.e., up to about 3% (w/v)) has been found to accelerate the phase transition from the initial thin phase to the final thin phase. The addition of water also helps in improving the filtration characteristics of the crystal slurry and the overall yield of the product.

The present invention is further described by reference to the working Examples. The Examples are provided for the purpose of illustrating the present invention and should not be construed as being a limitation on the scope or spirit of the invention. It should be understood that there may be other embodiments which fall within the spirit and scope of the invention as defined by the claims appended hereto.

EXAMPLE 1

Preparation of Paclitaxel Analogue III from Taxane Precursor IV

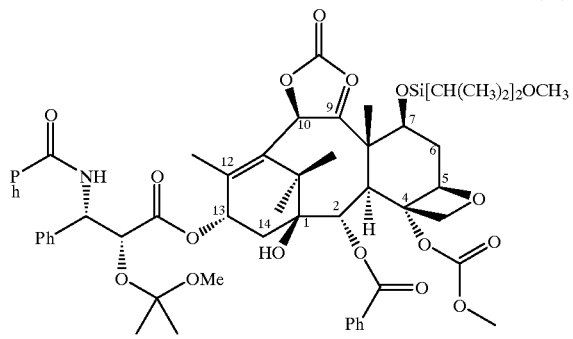

(IV)

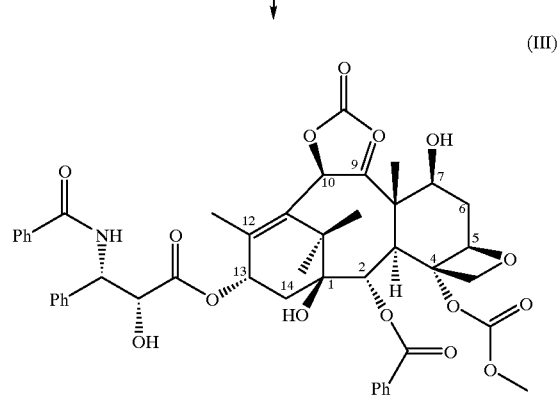

(III)

To a solution of taxane precursor IV in acetic acid (69 mL) was added a solution of trifluoroacetic acid in acetic acid (39 mL, 1 mmol solution prepared by dissolving 23.4 g of trifluoroacetic acid in 120 mL of water and 69 mL of acetic acid) at ambient temperature. Reaction mixture was stirred for 17 h and quenched with 40% aqueous sodium acetate solution (6 equiv). Reaction mixture was stirred for 20 min followed by the addition of dichloromethane (200 mL) and water (50 mL). The biphasic mixture was stirred for 20 min before separating the organic layer. Organic layer was washed with water (3×100 mL), dried (magnesium sulfate) and evaporated to afford 6.9 g of the crude product. Crystallization of the crude material from ethanol/heptane (1:1) gave 4.2 g (76%) of the title compound.

ESILRMS M+calcd. For C$_{47}$H$_{51}$NO$_{15}$: 869. Found 869; Anal calcd. For C$_{47}$H$_{51}$NO$_{15}$: C, 64.89; H, 5.91;N, 1.61. Found: C, 64.79: H, 5.82; N, 1.54.

EXAMPLE 2

Preparation of Paclitaxel from Taxane Starting Material V

[2aR-[2aα,4β,4aβ,6β,9α(4S*,5R*), 11α,12α,12aα,12bα]]-4,5-Dihydro-2,4-diphenyl-5-oxazolecarboxylic acid, 6,12b-bis(acetyloxy)-12-(benzoyloxy)-2a,3,4,4a,5,6,9,10,11,12,12a,12b-dodecahydro-11-hydroxy-4a,8,13,13-tetramethyl- 5-oxo-4-[(triethylsilyl)oxy]-7, 11 -methano-1H-cyclodeca[3,4]-benz[1,2-b]oxet-9-yl-ester

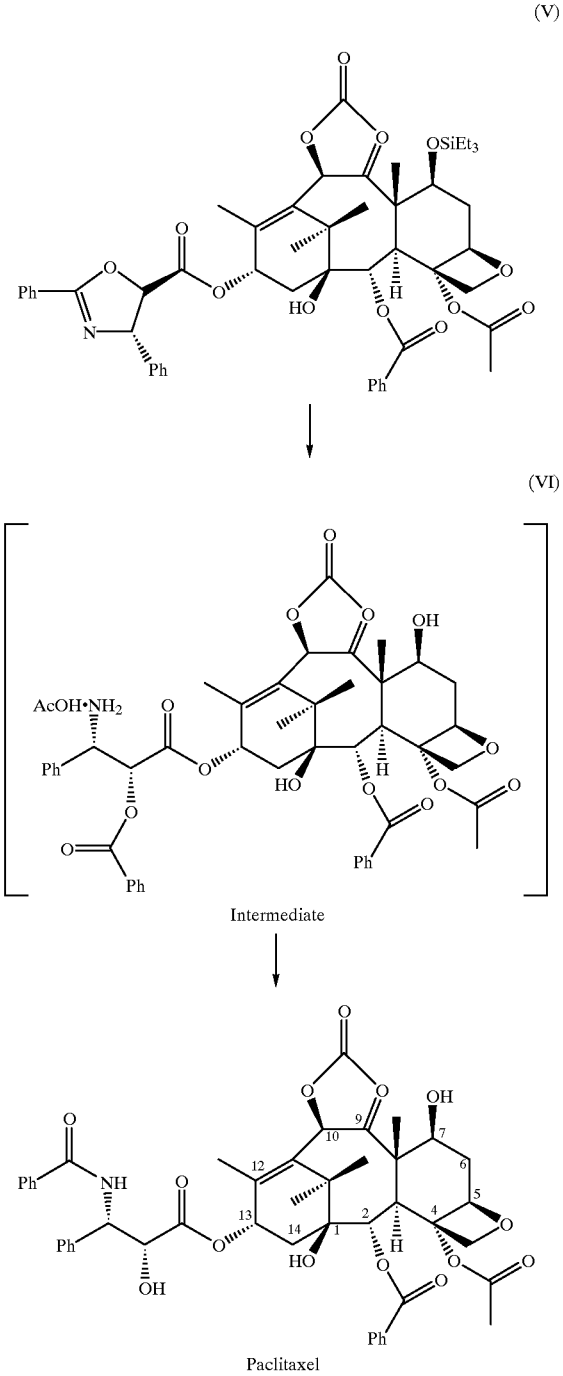

Taxane starting material V (15 g, 15.8 mmol) was dissolved in glacial acetic acid (129 mL). To this, a solution of trifluoroacetic acid (7.7 mL, 100 mmol) in glacial acetic acid (32 mL) and water (41 mL) was added at ambient temperature. After completion of reaction (5 to 7 hours), a solution of NaOAc (9 g, 109.7 mmol) in water (32 mL) was added to quench the reaction. Dichloromethane (146 mL) and water (100 mL) were added and the biphasic mixture was agitated for at least 15 minutes. The layers were separated and the spent aqueous layer was extracted with dichloromethane (100 mL). The rich dichloromethane layers were combined and washed three times with water (75 mL each) to give the paclitaxel-intermediate VI. Triethylamine (29.6 mL, 212.4 mmol) was added to the rich dichloromethane solution while maintaining the temperature at less than 25° C. After complete conversion of intermediate VI to paclitaxel (ca. 3 hours), a solution of sulfuric acid (25 mL) in water (225 mL) was added to quench the reaction while maintaining the temperature at less than 25° C. The layers were separated and the rich dichloromethane layer was washed several times with water (75 mL each) to remove residual acetic acid and triethylamine. The rich dichloromethane layer was solvent exchanged into isopropanol (ca. 300 mL) at no more than 40° C. The rich isopropanol solution was concentrated to ca. 227 mL at 25 to 40° C. The solution was heated to 48 to 52° C. to dissolve any precipitated paclitaxel. The water content of the isopropanol solution was adjusted to ca. 3% (w/v) with purified water and then slowly cooled to room temperature to initiate crystallization. After the conclusion of the thin-thick-thin phase transition of the crystal slurry, the slurry was further cooled to 0 to 5° C. to complete the crystallization. The crystal slurry was filtered, washed with cold isopropanol and dried in vacuo at less than 50° C. to afford 11.7 g (86.9 M%, HPLC area % 98.5) of paclitaxel.

What is claimed is:
1. A process for the preparation of paclitaxel or a paclitaxel analogue from a taxane precursor of formula I

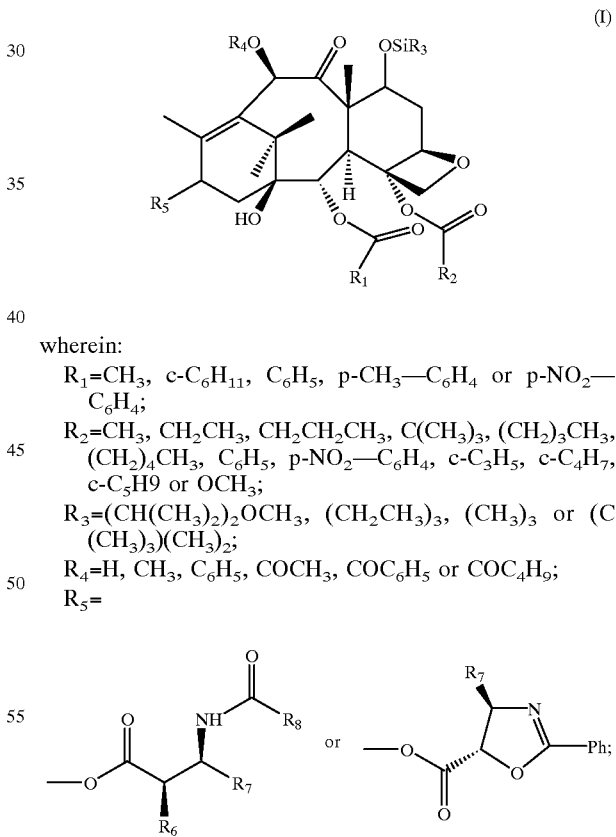

wherein:
$R_1$=$CH_3$, c-$C_6H_{11}$, $C_6H_5$, p-$CH_3$—$C_6H_4$ or p-$NO_2$—$C_6H_4$;
$R_2$=$CH_3$, $CH_2CH_3$, $CH_2CH_2CH_3$, $C(CH_3)_3$, $(CH_2)_3CH_3$, $(CH_2)_4CH_3$, $C_6H_5$, p-$NO_2$—$C_6H_4$, c-$C_3H_5$, c-$C_4H_7$, c-$C_5H9$ or $OCH_3$;
$R_3$=$(CH(CH_3)_2)_2OCH_3$, $(CH_2CH_3)_3$, $(CH_3)_3$ or $(C(CH_3)_3)(CH_3)_2$;
$R_4$=H, $CH_3$, $C_6H_5$, $COCH_3$, $COC_6H_5$ or $COC_4H_9$;
$R_5$=

$R_6$=H, F, OH, $OCH_3$, $OSi(CH_2CH_3)_3$, $OSi(C(CH_3)_3)(CH_3)_2$ or $OC(CH_3)_2OCH_3$, provided that $R_6$ is other than $OC(CH_3)_2OCH_3$ when $R_1$ is $C_6H_5$, $R_2$ is $CH_3$, $R_3$ is $(CH_2CH_3)_3$, $R_4$ is $COCH_3$, $R_7$ is $C_6H_5$ and $R_8$ is $C_6H_5$;
$R_7$=$C_6H_5$, $C(CH_3)_3$ or $CH(CH_3)_2$;

$R_8=C_6H_5$, $C(CH_3)_3$, $(CH_3)_3CO$, $(CH_3)_3CCH_2$, $CH_3(CH_2)_3O$, cyclobutyl, cyclohexyloxy or 2-furyl;

which process comprises the steps of:
(a) preparing a solution of taxane precursor in a weak organic acid;
(b) preparing a solution comprised of a strong acid in said weak organic acid and water;
(c) adding the solution from step (b) to step (a);
(d) stirring the reaction mixture formed in step (c);
(e) quenching said reaction mixture;
(f) adding water and extracting the product using an organic solvent;
(g) separating the organic layer from the aqueous layer; and
(h) isolating the product from said organic layer.

2. The process according to claim 1, wherein a compound of formula IV

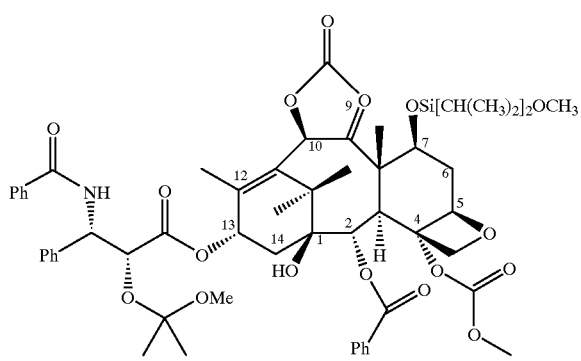

(IV)

is converted to a compound of formula III

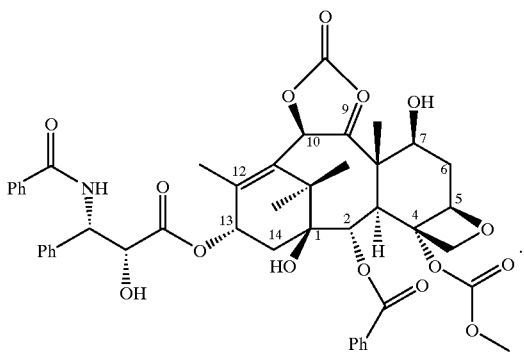

(III)

3. The process according to claim 1, wherein the weak organic acid is acetic acid or formic acid.

4. The process according to claim 3, wherein the weak organic acid is acetic acid.

5. The process according to claim 1, wherein the strong acid in step (b) is a mineral acid, a strong organic acid or a strong acid resin.

6. The process according to claim 5, wherein the strong acid is trifluoroacetic acid.

7. The process according to claim 1, wherein the volume ratio of the weak organic acid to the water in the reaction mixture is no more than about 3:1.

8. The process according to claim 1, wherein the quenching step (e) comprises a quenching reagent selected from the group consisting of sodium acetate, triethanolamine and diisopropylamine.

9. The process according to claim 8, wherein the quenching reagent is sodium acetate.

10. The process according to claim 1, wherein the organic solvent in said extraction step (f) is a water-immiscible solvent.

11. The process according to claim 10, wherein the organic solvent is selected from the group consisting of dichloromethane, ethyl acetate, methyl ethyl ketone and methyl isobutyl ketone.

12. The process according to claim 11, wherein the organic solvent is dichloromethane.

13. The process according to claim 1, wherein step (d) further comprises stirring the reaction mixture formed in step (c) at ambient temperature until the taxane precursor is consumed.

14. The process according to claim 1 for the preparation of paclitaxel or a paclitaxel analogue of formula II

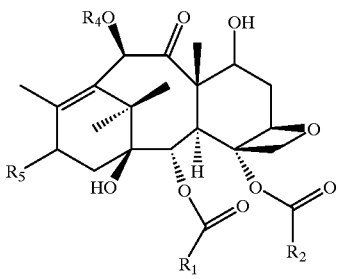

(II)

wherein:

$R_1=CH_3$, $c\text{-}C_6H_{11}$, $C_6H_5$, $p\text{-}CH_3\text{—}C_6H_4$ or $p\text{-}NO_2\text{—}C_6H_4$;

$R_2=CH_3$, $CH_2CH_3$, $CH_2CH_2CH_3$, $C(CH_3)_3$, $(CH_2)_3CH_3$, $(CH_2)_4CH_3$, $C_6H_5$, $p\text{-}NO_2\text{—}C_6H_4$, $c\text{-}C_3H_5$, $c\text{-}C_4H_7$, $c\text{-}C_5H_9$ or $OCH_3$;

$R_4=H$, $CH_3$, $C_6H_5$, $COCH_3$, $COC_6H_5$ or $COC_4H_9$;

$R_5=$

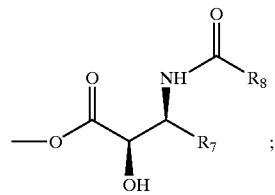

$R_7=C_6H_5$, $C(CH_3)_3$ or $CH(CH_3)_2$; and $R_8=C_6H_5$, $C(CH_3)_3$, $(CH_3)_3CO$, $(CH_3)_3CCH_2$, $CH_3(CH_2)_3O$, cyclobutyl, cyclohexyloxy or 2-furyl.

15. The process according to claim 1, wherein a compound of formula V

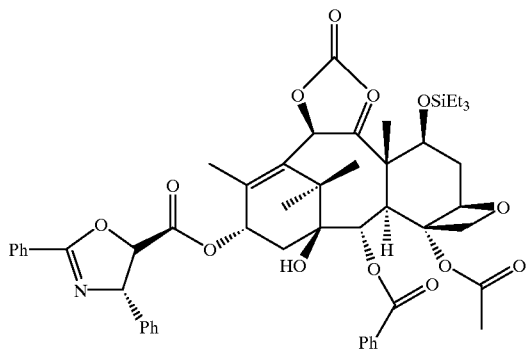

(V)

is converted to a paclitaxel intermediate of formula VI

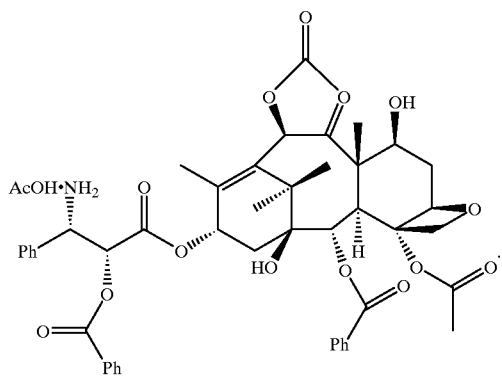

(VI)

16. The process according to claim 1, wherein the product of steps (a) to (g) is paclitaxel and wherein the step (h) isolation comprises a solvent exchange of the organic layer from step (g) into a crystallization solvent suitable for the crystallization of paclitaxel in Form A or Form B.

17. The process according to claim 16, wherein the solvent for the crystallization of paclitaxel in crystal Form A is comprised of a two solvent system with hepane as the non-solvent and ethyl acetate, acetone, ethanol or isopropanol as the solvent.

18. The process according to claim 16, wherein the solvent for the crystallization of paclitaxel in crystal Form A is isopropanol.

19. The process according to claim 16, wherein the solvent for the crystallization of paclitaxel in crystal Form B is comprised of a two solvent system with water as the non-solvent and acetic acid, acetone, methanol, ethanol, isopropanol, tetrahydrofuran or acetonitrile as the solvent.

20. The process according to claim 16, wherein the solvent for the crystallization of paclitaxel in crystal Form B is acetone and water.

21. The process according to claim 16, wherein the solvent for the crystallization of paclitaxel in crystal Form B is acetic acid and water.

22. The process according to claim 18, wherein the water content of the crystallization solution in isopropanol may be up to about 3% (w/v) for the isolation of paclitaxel in crystal Form A.

23. The process according to claim 18, wherein the paclitaxel Form A undergoes a crystal slurry phase transition which is accelerated by the presence of up to about 3% (w/v) water in said crystallization solvent.

24. The process according to claim 18, wherein the yield of the paclitaxel Form A is increased by the presence of up to about 3% (w/v) water in said crystallization solvent.

* * * * *